United States Patent [19]
Ahmad et al.

[11] Patent Number: 6,139,848
[45] Date of Patent: Oct. 31, 2000

[54] PERSONAL LUBRICANT COMPOSITIONS

[75] Inventors: Nawaz Ahmad, Monmouth Junction; Kalpana Patel, West Windsor; Mark Huseth, Somerset, all of N.J.

[73] Assignee: McNeil-PPC, Inc., Skillman, N.J.

[21] Appl. No.: 09/501,080

[22] Filed: Feb. 9, 2000

Related U.S. Application Data

[60] Provisional application No. 60/119,949, Feb. 12, 1999.

[51] Int. Cl.⁷ ..................................................... A61K 9/00
[52] U.S. Cl. .......................... 424/400; 508/307; 514/841; 514/944; 424/401; 424/DIG. 14
[58] Field of Search ............................ 508/307; 424/400, 424/401, DIG. 14; 514/841, 944

[56] References Cited

U.S. PATENT DOCUMENTS

| | | | |
|---|---|---|---|
| 4,410,517 | 10/1983 | Stillman | 508/307 |
| 4,482,537 | 11/1984 | El-Menshawy et al. | 424/60 |
| 4,851,434 | 7/1989 | Deckner | 514/625 |
| 4,952,560 | 8/1990 | Kigasawa et al. | 514/773 |
| 4,999,342 | 3/1991 | Ahmad et al. | 514/843 |
| 5,425,938 | 6/1995 | Znaiden et al. | 424/78.02 |
| 5,514,698 | 5/1996 | Ahmad et al. | 514/396 |
| 5,885,591 | 3/1999 | Ahmad et al. | 424/400 |

*Primary Examiner*—Jacqueline V. Howard

[57] ABSTRACT

A stable personal lubricant composition containing at least one water soluble polyhydric alcohol, a water soluble polymer derived from cellulose, tocopherol or a tocopherol derivative, an emulsifier and water.

11 Claims, 15 Drawing Sheets

Lubricity Comparison of Sylk™, and Senselle™ with K-Y Liquid®.

FIG. 15

PERSONAL LUBRICANT COMPOSITIONS

This application claims benefit of provisional application 60/119,949, Feb. 12, 1999.

BACKGROUND OF THE INVENTION

Field of the Invention

This invention relates to stable personal lubricant compositions containing tocopherol and related compounds as microemulsions. They are at least three times more lubricious than the compositions known previously. The compositions of this invention can provide a vehicle for delivering moisture, tocopherol and related tocopherol compounds such as topcopherol acetate and other medicaments for contraception and for the treatment and prevention of disease to the skin and mucous membrane especially the vaginal mucosa. This invention also relates to methods of preparation and use of the personal lubricant compositions of this invention.

SUMMARY OF THE INVENTION

This invention relates to stable personal lubricant compositions containing tocopherol and related compounds such as tocopherol acetate in the form of a microemulsion. The compositions of this invention are pourable liquids or pourable low viscosity microemulsions which adhere to the mucous membranes and provide or add lubricity, moisture and tocopherols to these membranes such the oral, rectal or vaginal mucosa. Furthermore, the compositions of this invention, while lubricious, are not readily washed off the mucosal membranes. Not only are the compositions of this invention highly lubricious, they may contain tocopherol and related compounds in the form of a microemulsion and are surprisingly physically stable, i.e., the tocopherol which constitutes the oil phase or internal phase of these compositions does not separate from the aqueous phase of the composition. It is believed that the physical stability and high lubricity of the compositions of this invention are due to the novel ratios between the elements of the compositions. By making compositions within the scope of this invention, surprisingly high lubricity values and physical stability have been achieved The compositions of this invention preferably contain at least one water soluble polyhydric alcohol, a water-soluble polymer derived from cellulose, tocopherol or a tocopherol derivative, a nonionic water soluble or dispersible emulsifier, preferably a polyalkylene emulsifier, most preferably an emulsifier chosen from the group consisting of polyoxyethylene (20) sorbitan monostearate commonly known as Tween 60 or Polysorbate 60 or polyethylene glycol ether of isocetyl alcohol (commonly known as Isoceteth 20 or Arlasolve 200, which is available from ICI Americas. Inc, New Castle, Del.), and water. The water-soluble polyhydric alcohol serves to increase the lubriciousness of the compositions. The water-soluble cellulose-derived polymer serves to impart the desired slipperiness and viscosity to the composition. Water is desired in sufficient quantity to be delivered as moisture to the mucous membranes and to provide consistency and viscosity to the composition. The nonionic surfactants used in this invention emulsify tocopherol, tocopherol acetate or other tocopherol derivatives into a microemulsion in which the internal or oil phase is reduced to very small globules measuring 2 or less than 2 microns in size. Due their immensely small size the emulsion globules do not coalesce and serve to assist in maintaining the homogeneity of the emulsions and preserve physical stability of the compositions of this invention.

Preferably, the ratio of the tocopherol or tocopherol derivative present in the compositions of this invention to the emulsifier is from about 1:5 to about 1:30, preferably from about 1:5 to about 1:20. This is unusual in view of previous formulations as the level of emulsifier is relatively high, which is considered quite irritating. However, in the compositions of this invention, the high level of emulsifier does not produce significant irritation.

The process for preparing the microemulsions of this invention has been specially designed to limit the amount of thermal and mechanical energy expended in the production of the emulsions. The small amount of internal phase in the emulsification stage results in considerable reduction in energy requirements and overall processing time. This is accomplished by heating both the oil phase, which in this case is preferably tocopherol or tocopherol acetate, and a portion of the water or external phase along with the emulsifier to the required temperature to form a concentrated emulsion. The balance of the aqueous phase is then added at a considerably lower or room temperature during the cooling state. The energy required to heat the aqueous phase and the mechanical energy of emulsifying the entire emulsion and mixing during the cooling stage are considerably reduced. The homogenizing agents or emulsifiers assist in the formation and maintaining physical stability once the emulsion has been subjected to fine-screen mixing and conversion to a microemulsion.

The pH of the compositions of this invention should be adjusted to be compatible with the pH of the biomembrane to which they will be delivered. An inorganic base may be used to adjust the pH. The quantity of water in the compositions may also be adjusted in order to achieve the appropriate pH.

DETAILED DESCRIPTION OF THE PREFERRED EMBODIMENTS

Preferably, the compositions of this invention contain at least one polyhydric alcohol which is water-soluble, a water-soluble polymer derived from cellulose, tocopherol or a tocopherol derivative, a polyalkylene glycol ether of a branched-chain aliphatic alcohol having from 6 to 18 carbon atoms in the chain and water. The water-soluble polyhydric alcohol portion of the compositions may contain one or more polyhydric alcohols. Preferably, the polyhydric alcohol portion should contain glycerin, propylene glycol, sorbitol or a combination thereof. Of course, other polyhydric alcohols known to those of ordinary skill in the art may be used in the products of this invention, such as, for example, polyethylene glycol ranging from molecular weight of from about 300 to about 1450.

The polyhydric alcohol portion of the product should make up from about 5 to about 90% by weight of the composition. More preferably, the compositions of this invention should contain a combination of two or more polyhydric alcohols and one or more cellulose gums. Most preferably, the polyhydric alcohol portion of the composition should contain glycerin, propylene glycol and/or sorbitol in combination. Preferably, there should be from about 5 to about 50% by weight of glycerin and from about 2 to about 40% by weight of propylene glycol. Preferably, sorbitol is also used in the compositions and can range from about 5% to about 20% by weight of the composition The compositions of this invention should also contain one or more water-soluble cellulose-derived polymers. The polymer is preferably cellulose gum such as hydroxyethylcellulose, although other polyols known to those of ordinary skill in the art may be used, such as carboxymethylcellulose, hydroxypropylcellulose and hydroxypropylmethylcellulose and the like. Preferably, a combination of gums and one of the polyhydric alcohols should be used, with one element being present in a significantly greater amount (polyhydric alcohol) than the other (cellulose gum). More preferably, the polyhydric alcohol is glycerin. Preferably, the gum is hydroxyethylcellulose.

It should be noted that raising the cellulose gum level decreases lubricity of the compositions. There is an optimum concentration of cellulose gum that imparts lubricity. Increasing the cellulose gum concentration increases or results in increase in the viscosity of the composition which increases the coefficient of friction and thereby decreases the lubricity. The polyol should be present in the compositions of this invention in the amount of from about 5 to about 45% by weight of the composition. The gum should be present in the compositions of this invention in the amount of from about 0.1% to about 2% by weight of the composition. More preferably, it should be present in the amount of from about 0.25% to about 1%.

An inorganic base may be used to adjust the pH of the composition to be compatible with the vaginal, rectal or oral membranes. Potassium hydroxide or another alkali metal or alkaline earth metal base may be useful to provide the appropriate pH. Of course, any other physiologically acceptable base may also be utilized in this manner. From about 0.05 to about 5% by weight inorganic base is preferably used.

The tocopherol or tocopherol derivative useful in the compositions of this invention is preferably tocopherol acetate, although other ester derivatives may preferably be used as well as tocopherol acid succinate and other tocopherols. The tocopherol or tocopherol derivative should be present in an amount of from about 0.001 to about 5% by weight of the composition. More preferably, the tocopherol or tocopherol derivative is present in an amount of from about 0.05 to about 2% by weight of the composition.

A preservative may be important for use in the products of this invention, in order to preserve the stability of the compositions of this invention and to prevent the growth of microorganisms therein. The preservative portion of the compositions of this invention may be one or more known preservatives, such as methylparaben, benzoic acid, sorbic acid, gallic acid or propylparaben. From about 0.05% to about 0.75% by weight preservative should be used.

Water functions to provide the appropriate pH, consistency and viscosity to the composition. The compositions of this invention can be used to moisturize mucous membranes by delivering water as moisturizer.

The compositions of this invention may also be used to convey medication or other treatment agents to the biomembranes, such as contraceptives, antimicrobial agents and the like. Contraceptives may include nonoxynol-9, octoxynol-9 and menfegol. Antifungal agents include imidazole compounds such as miconazole, econazole, terconazole, saperconazole, itraconazole, butaconazole, dotrimazole, tioconazole and ketoconazole and the like. Antibacterial agents may also be present such as metronidazole, chlorhexidine gluconate and hydrogen peroxide. The compositions of this invention may also be used to deliver buffering agents to adjust the pH of the membranes in order to promote healthy environments. From about 2 to about 20% contraceptives may be present in the compositions of this invention. From about 1 to about 10% antifungal agents may be used; from about 0.5% to about 10% antibacterial compounds or buffer system may preferably be used.

The compositions of this invention should be prepared as follows: to a first container should be added one or more polyhydric alcohols, e.g., glycerin and propylene glycol, and preservatives, if desired. The mixture should be heated to about 55 to about 65° C., preferably 60° C. and mixed with a paddle blade. When the temperature of the mixture reaches about 60°, tocopherol or its derivative should be added with the polyalkylene glycol ether of a branched-chain aliphatic alcohol. The composition should be mixed for about 10 to about 20 minutes, preferably 15 minutes, maintaining the temperature at about 60° C. After 15 minutes, it should be verified that all solid materials have dissolved and the mixture then cooled to from about 40° C. to about 50° C., preferably about 45° C. When the mixture has cooled, the cellulose compounds should be added and the composition mixed until free of lumps. When free of lumps, water, polyhydric alcohol and inorganic base should be added and the composition mixed for about one hour at slow speed at a temperature of about 40° C. to about 50° C., preferably about 45° C. A smooth syrupy liquid is formed.

The resultant compositions also have a very high degree of clarity. Measured in accordance with standard turbidimetric procedures, they should have a turbidity of less than about 2. Turbidity of the product may be determined using Model 2100N Laboratory Turbidimeter sold by Hach Company. The instrument uses light scattering for turbidity determination. The more light is scattered by the product, the more turbid it is. Concomitantly, the lower the reading from the instrument, the less turbid the product is. The turbidity of the compositions of this invention range from 1.71 to 1.96 and are generally less than about 2. Clarity, which is a measurement indirectly proportional to turbidity, may be obtained by subtracting the turbidity measurement from 100%. For the compositions of this invention, the clarity should be at least about 98%.

The following examples serve to illustrate the compositions and methods of this invention. However, they are not presented in order to limit the scope of the invention in anyway.

EXAMPLE 1

A composition in accordance with this invention was made having the following ingredients:

| Ingredient | Amount |
|---|---|
| Glycerin, USP | 30.000 |
| Propylene Glycol, USP | 5.000 |
| Sorbitol Solution, USP | 10.000 |
| Methylparaben, USP | 0.200 |
| Benzoic Acid, USP | 0.200 |
| Hydroxyethylcellulose, NF (Natrosol 250H) | 0.450 |
| Sodium Hydroxide, NF | 0.015 |
| Vitamin E Acetate | 0.100 |
| Arlasolve 200 | 2.000 |
| Purified Water, USP | 52.035 |
| Total | 100.000 |

This formulation was made by adding glycerin, propylene glycol, methylparaben and benzoic acid to a container, heating the mixture to 60° C. while mixing with a Lightning® mixer and mixed with a paddle blade. When the temperature of the mixture reached 60° C., vitamin E acetate and Arlasolve 200 were added. Mixing was continued for 15 minutes at the same temperature. After 15 minutes, it was verified that all solid materials were dissolved. The mixture was then cooled to 45° C. At this temperature, hydroxyethylcellulose (Natrosol 250H) was added and the composition mixed until free of lumps. When free of lumps, purified water, sorbitol solution and sodium hydroxide were added and the mixing continued for 60 minutes at a slow (200 rpm) speed maintaining a temperature of about 45° C. A smooth syrupy liquid was formed.

EXAMPLE 2

A composition in accordance with this invention was made using the method set forth below. The composition had the following components:

| % W/W | INGREDIENTS | Theoretical Amt. |
|---|---|---|
| 35.000 | Propylene Glycol, USP | 525.000 |
| 10.000 | Sorbitol Solution, USP | 150.000 |
| 0.200 | Methylparaben, USP | 3.000 |
| 0.200 | Benzoic Acid, USP | 3.000 |
| 0.450 | Hydroxyethylcellulose, NF (Natrosol 250H) | 6.750 |
| 0.100 | Vitamin E Acetate | 1.500 |
| 0.500 | Polysorbate 60 (Tween 60) | 7.500 |
| 5.035 | Purified Water, USP (#4) | 75.525 |
| 48.515 | Purified Water, USP (#3) | 727.725 |
| 100.000% | Total | 1500.000gms |

Figure 15:
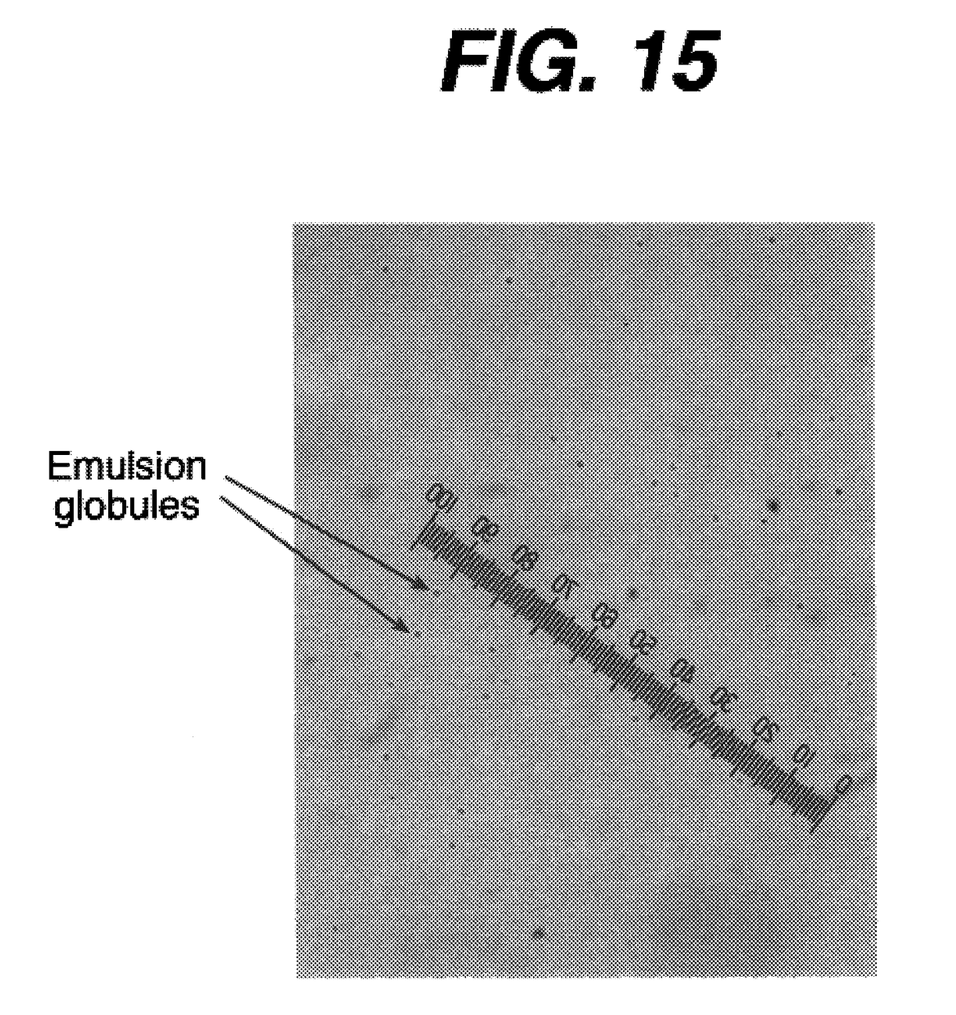
FIG. 15 is a photomicrograph of microemulsion prepared in accordance with this invention depicting globules of tocopherol acetate. Each division on the scale is equal to 2 microns.

To a container was added Propylene Glycol, Methylparaben, and Benzoic Acid. The container was heated to 60° C. while mixing with a Lightning® mixer and paddle blade. Mixing was continued for 15 minutes, maintaining the temperature at about 60° C. After 15 minutes, it was verified that all solid materials were dissolved, then the mixture was cooled to 45° C. When cooled to 45° C. hydroxyethylcellulose (Natrosol 250H) was slowly added and the composition mixed until free of lumps. When free of lumps, Purified Water was added. To a separate container was added Vitamin E Acetate, Sorbitol solution and Polysorbate 60 and the container heated to 45° C. When the temperature reached 45° C. mixing was begun with a Silverson® Homogenizer using the finest screen and approximately 5% of the total water was added to the composition. The composition was mixed for about 3 minutes. The mixture in the second container was then added to the mixture in the first container and the resultant composition mixed for 5 minutes (or until uniform) with the Silverson® Homogenizer. After product was uniform mixing was continued for 60 minutes with the Lightning Mixer at a slow speed maintaining a temperature of 45° C. A smooth syrupy liquid was formed. FIG. 15 is a photomicrograph depicting the microemulsion composition of this invention.

EXAMPLE 3

A standard test method to determine and compare the degree of lubricity of personal lubricants does not exist. Lubricants work by reducing the friction between two surfaces. Certain instruments are available that can determine the force to move one surface horizontally across another surface. While accomplishing this procedure, a certain amount of pressure can also be applied by placing a weight on the upper moving surface. By applying a lubricant sample between these two surfaces, the force required to move the surface in the presence of a particular lubricant can be determined. From this force and weight, a coefficient of friction value for a lubricant can be calculated. The coefficient of friction is inversely proportional to the lubricity of a product and is known as "relative lubricity". Relative lubricity can be calculated from the coefficient of friction data by dividing one (1) by the corresponding coefficient of friction value. An instrument, namely Coefficient of Sliding Friction Rig adapted to a Texture Analyzer, marketed by Texture Technologies Corp., 18 Fairview Road, Scarsdale, N.Y. was used for determining relative lubricity of several lubricant products in comparison with that of the compositions of this invention. The equipment contains a platform having a friction sledge attached to a load cell which is constrained to slide across the platform over which a test sample is applied. Load is provided by a 430 g precision weight positioned centrally over the sledge. This arrangement offers the advantage of measuring coefficient of sliding friction in both directions such that data for the "push" and the "pull" phases of the test can be generated over a fixed period of time. For this study, it was possible to generate coefficient of friction data for an extended period of five (5) minutes. In making the measurements set forth in FIGS. 2–11 a non-lubricated condom was mounted over the sledge, a thin film of the lubricant sample was applied over the fixed platform and coefficient of sliding friction readings were recorded over a five-minute period while the friction sledge went back and forth from the starting point. The coefficient of friction data, therefore, has negative (−) sign during the "push" phase and positive (+) sign during the "pull" phase of the experiment. Coefficient of friction data for the baseline, with no product applied to the condom was also generated for comparison. Relative lubricity data presented in the plots in FIGS. 2–11 was calculated from the coefficient of friction data generated by the instrument. The following products were tested in this study K-Y Liquid® (manufactured by Advanced Care Products, Personal Products Company, Skillman, N.J.), Astroglide™ (Lot #96056, manufactured by BioFilm, Inc. Vista, Calif. 92083), WET Original™ (Lot # NU1164, distributed by WET Formulas International, North Hollywood, Calif. 91605), WET Oil™ (Lot # L12034, distributed by WET Formulas International, North Hollywood, Calif. 91605), WET Light™ (Lot WET Light™ (Lot # NU1144, distributed by International, North Hollywood, Calif. 91605), ForPlay™ (Lot# EX1100, distributed by Trimensa Pharmaceuticals, Newbury Park, Calif. 91320-1301), ForPlay™ with Nonoxynol-9 (Lot# EX1100, distributed by trimensa Pharmaceuticals, Newbury Park, Calif. 91320-1301), Vagisil™ Intimate Moisturizer (Lot# R6M020, manufactured by COMBE Incorporated, White Plains, N.Y. 10604), Aqua Lube™ (Lot #4542, distributed by Mayer Laboratories, Inc., Oakland, Calif. 94607), PROBE™ (Lot # 7348, distributed by Davryan laboratories, Inc. Portland, Oreg. 97201-1850), EROS™ (Lot# 329512, distributed by CDC Distribution center, Fleishstrabe 53, Germany). Texture Analyzer TA-XT2I (SID 41) was utilized for the test, having a Plexi-glas™ plate 3"×4"×⅜" in size, a 430 g weight and a 6.0 mil Bird Applicator. The substrate used was a polyethylene/foil liner and a Trojans® non-lubricated condom. The texture analyzer settings were as follows: Test Mode and Option, Measure Force In tension, Cycle Until Count, Trigger, Type-Button, Stop Plot at—Trigger Return, Brea—Detect off, level. The pre-test speed was 0 mm/s, the test speed was 2.0 mm/s, the post test speed was 0.0 mm/s and the distance traveled was 40.0 mm. The test was run for 300 seconds. The PE/foil liner was glued to the aluminum base or platform of the Texture Analyzer. The Plexi-glas™ sled was covered with the condom, a 6.0 mil film of test product was cast onto the liner and the 430 g weight placed on the center of the sled. The test was run and the results plotted as a graph. FIGS. 2–11 depict the graphed results of tests comparing K-Y Liquid® with commercially-available samples. The data indicate that the K-Y Liquid® lubricant has a higher lubricity and is longer lasting during the 300 second test period than the comparative products. Preferably, the lubricity of the compositions of this invention is at least 30.

EXAMPLE 4

Figure 1:
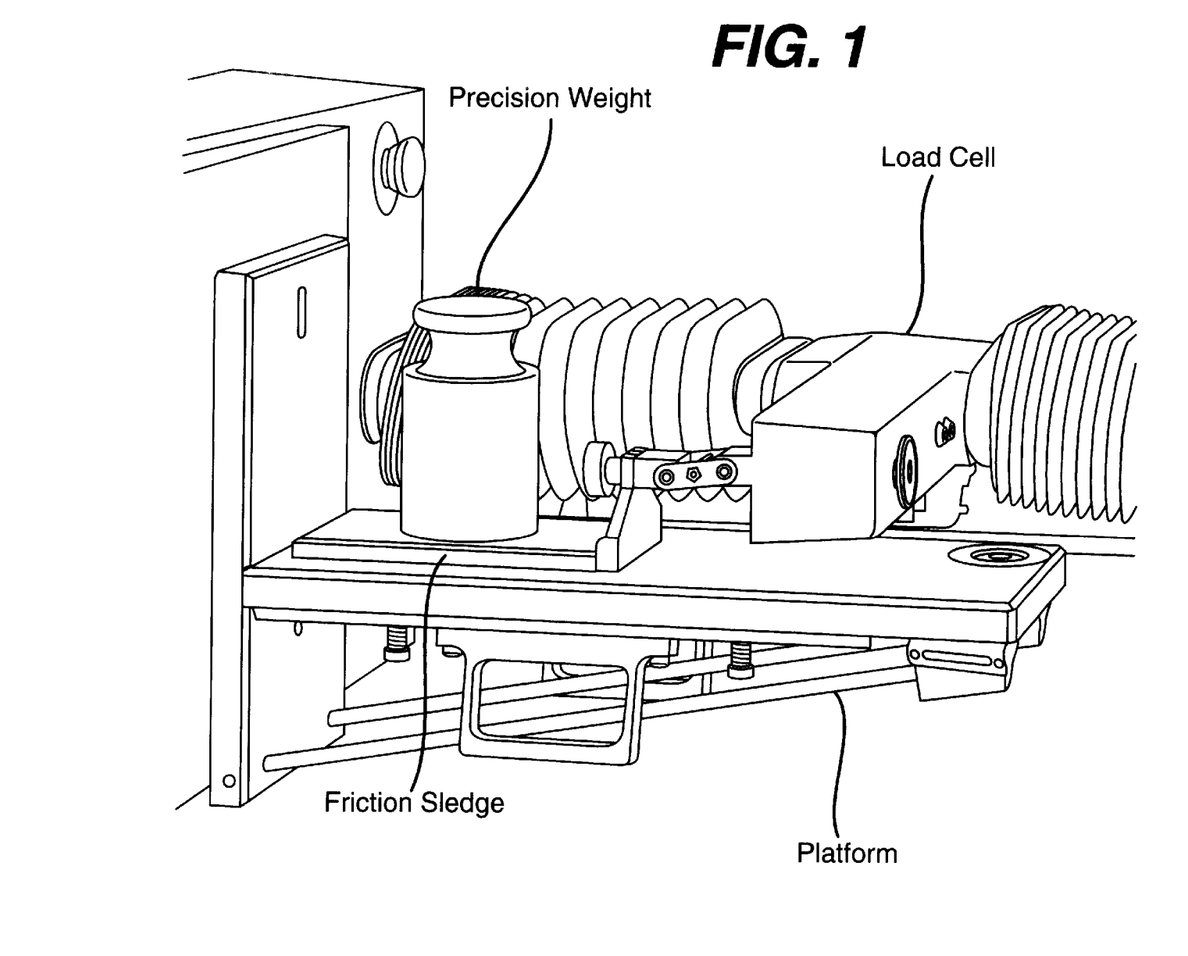
FIG. 1 is a frontal view of a device used to test coefficient of friction.
Figure 2:
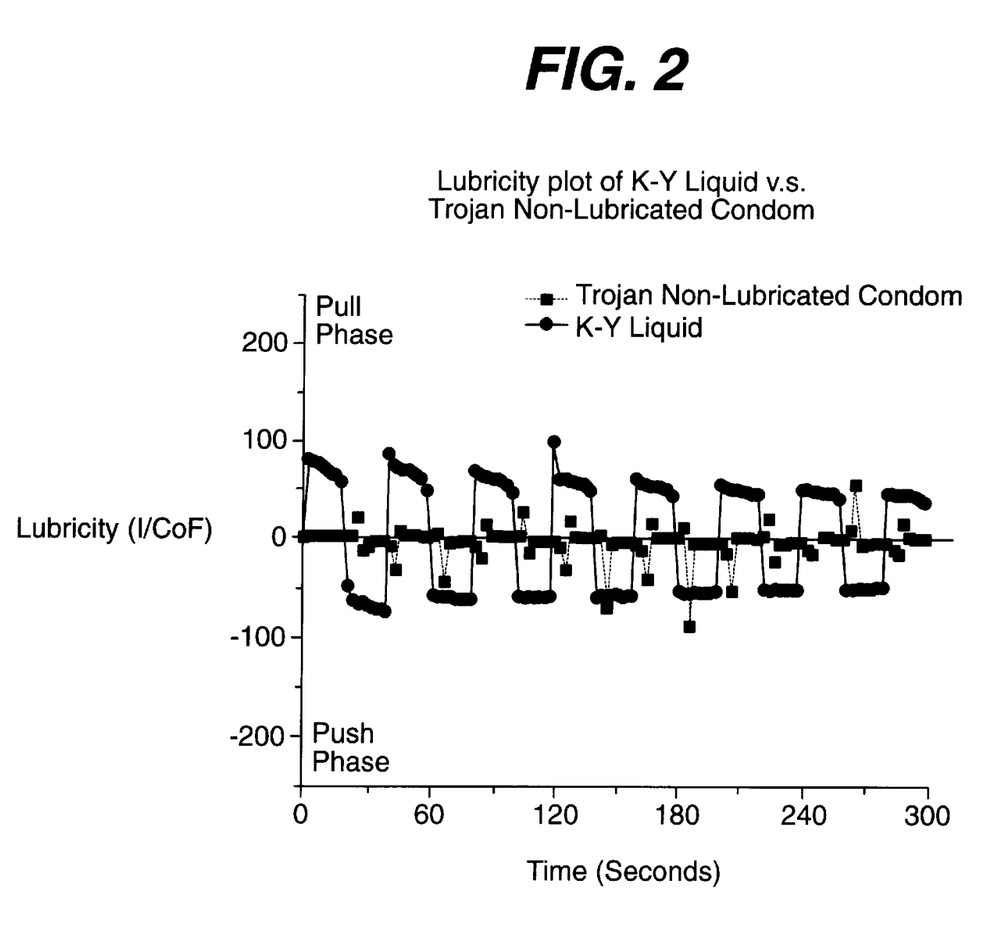
FIGS. 2–11 are graphs depicting the Relative Lubricity of a number of test samples, including a composition described U.S. Pat. No. 5,885,591.
Figure 3:
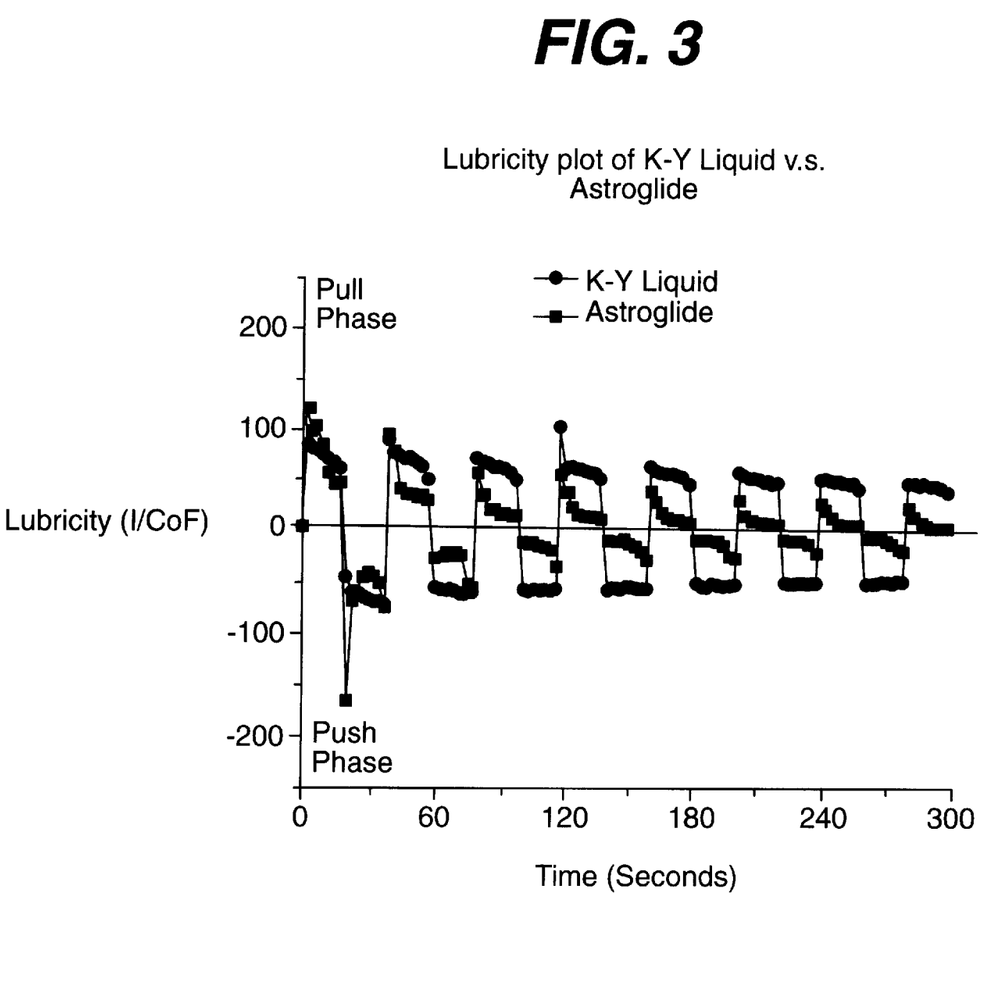
Figure 4:
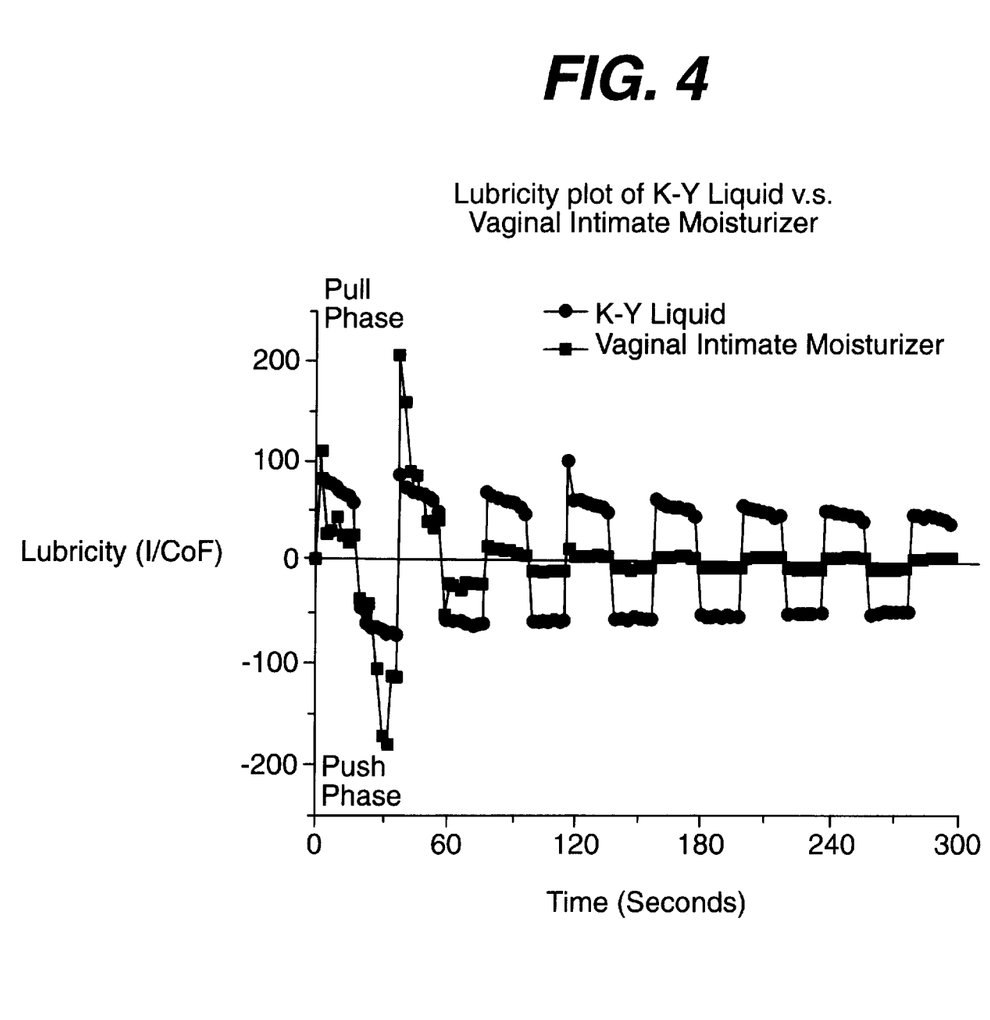
Figure 5:
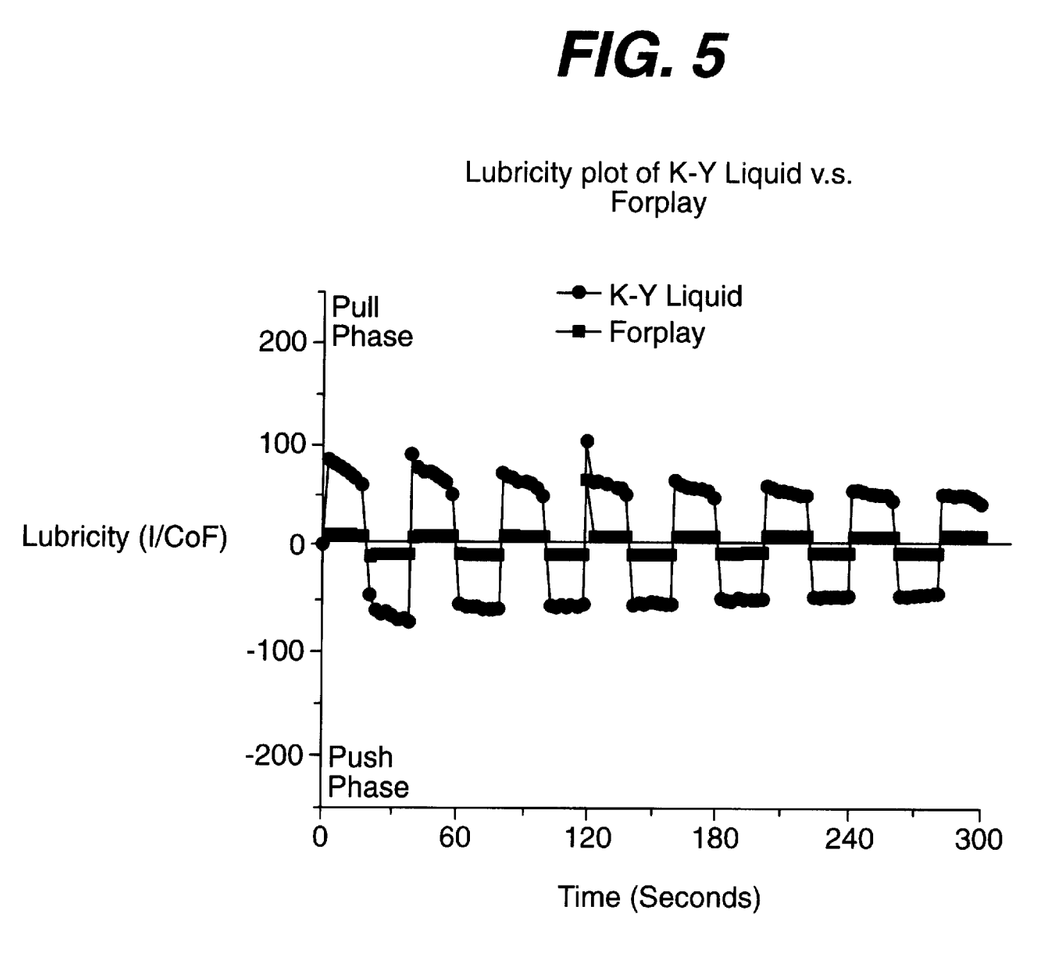
Figure 6:
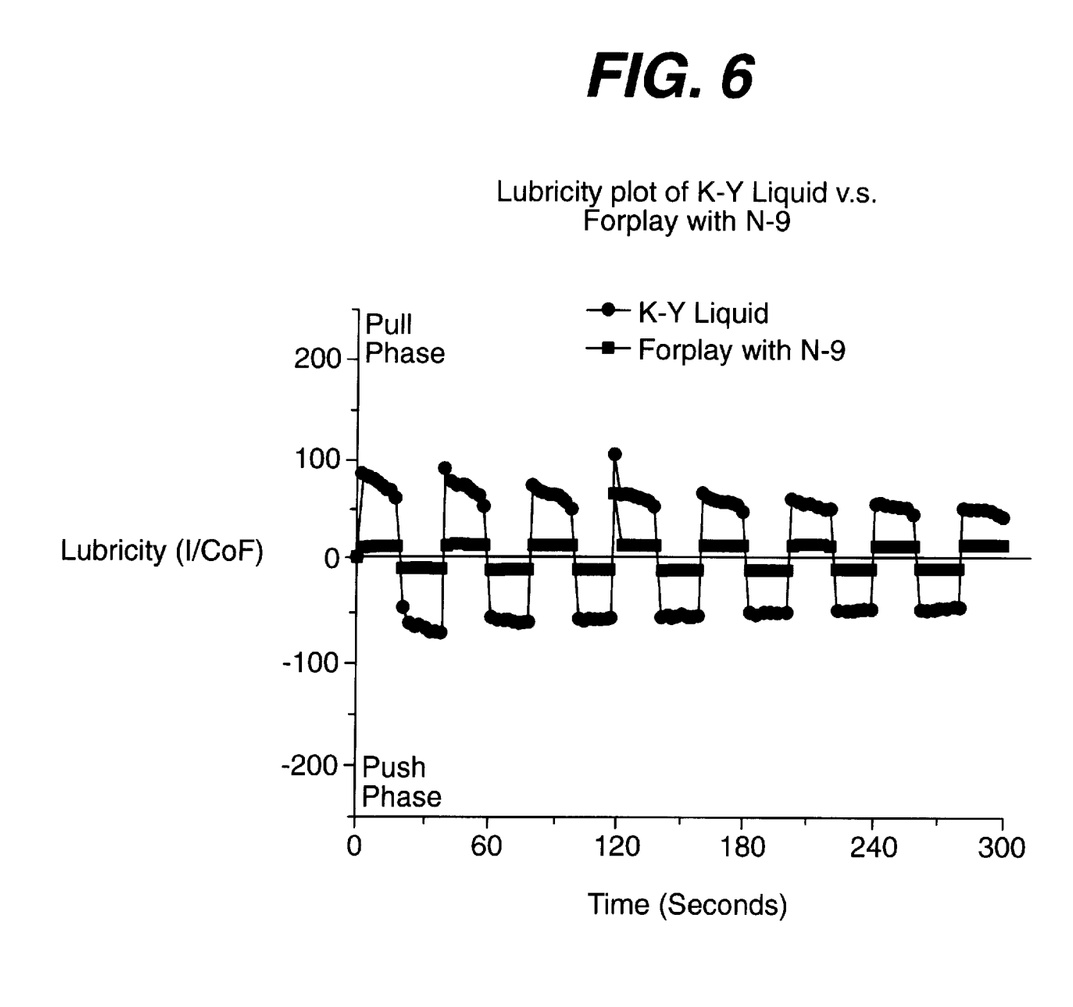
Figure 7:
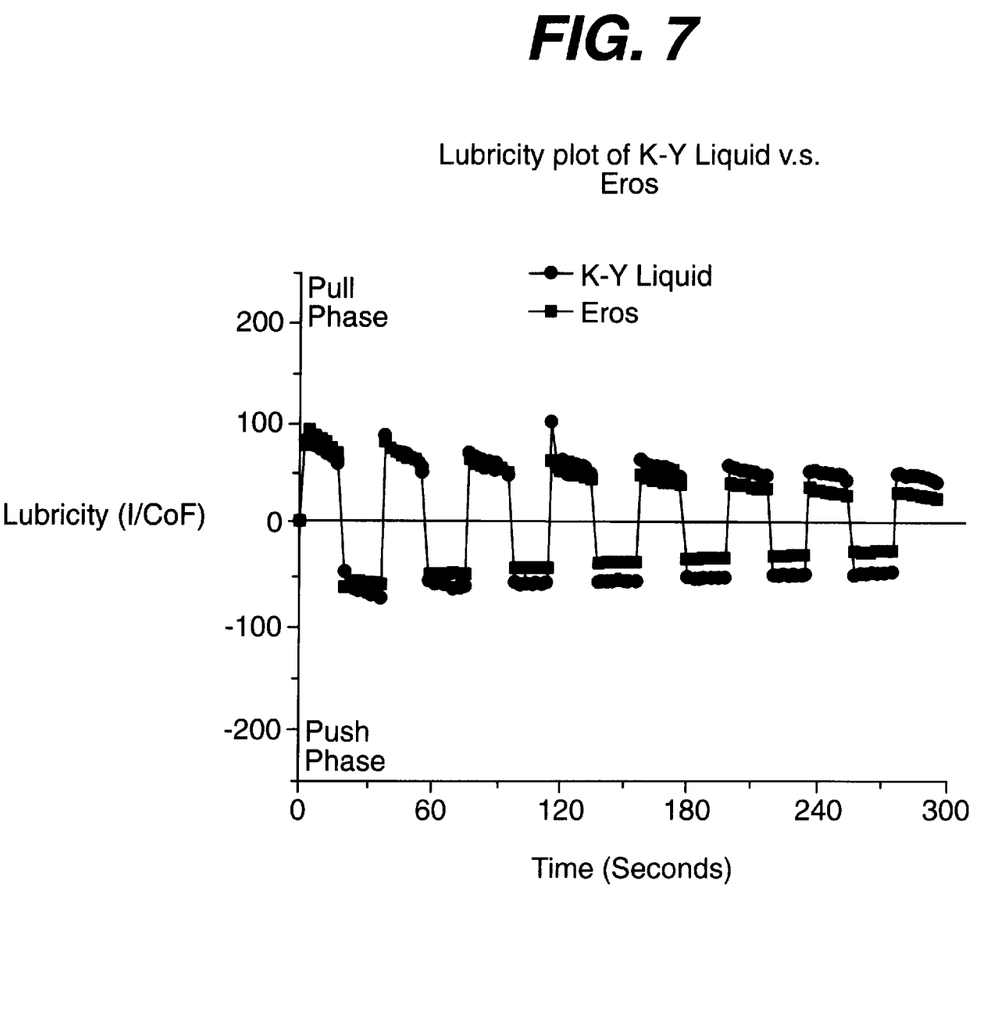
Figure 8:
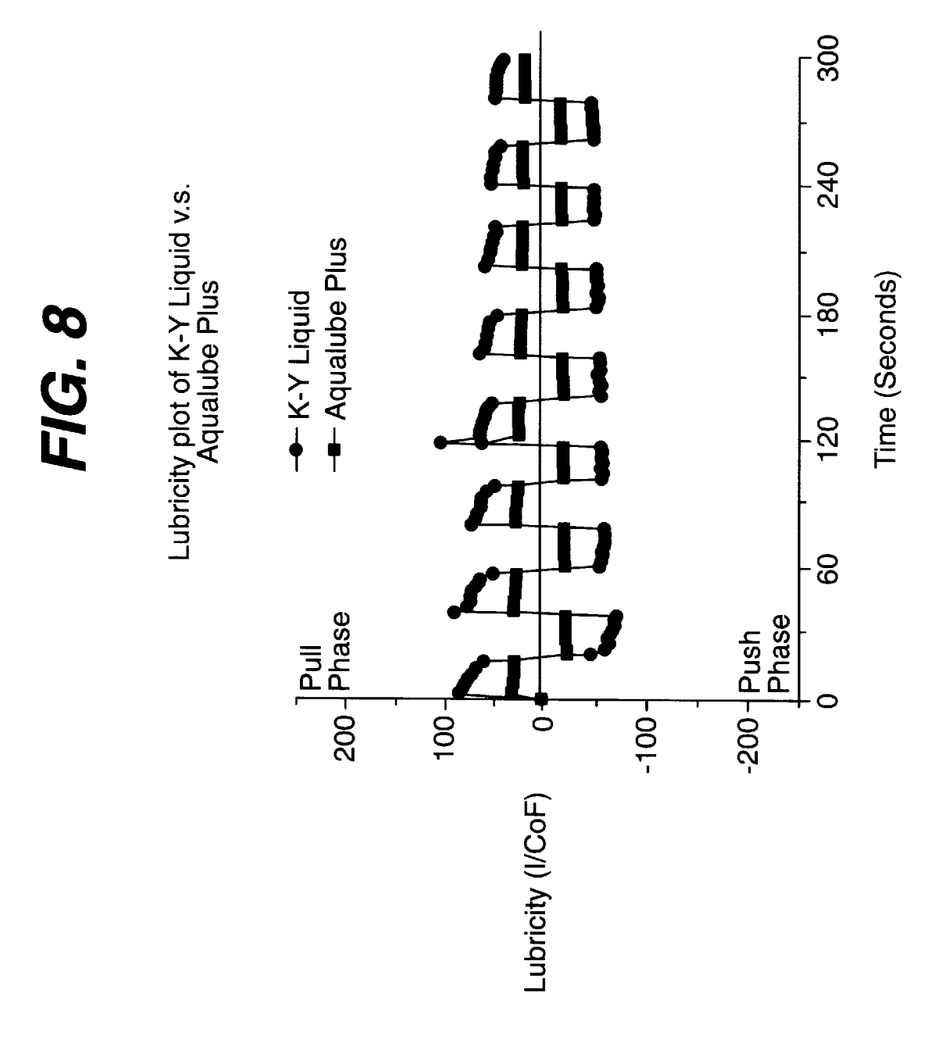
Figure 9:
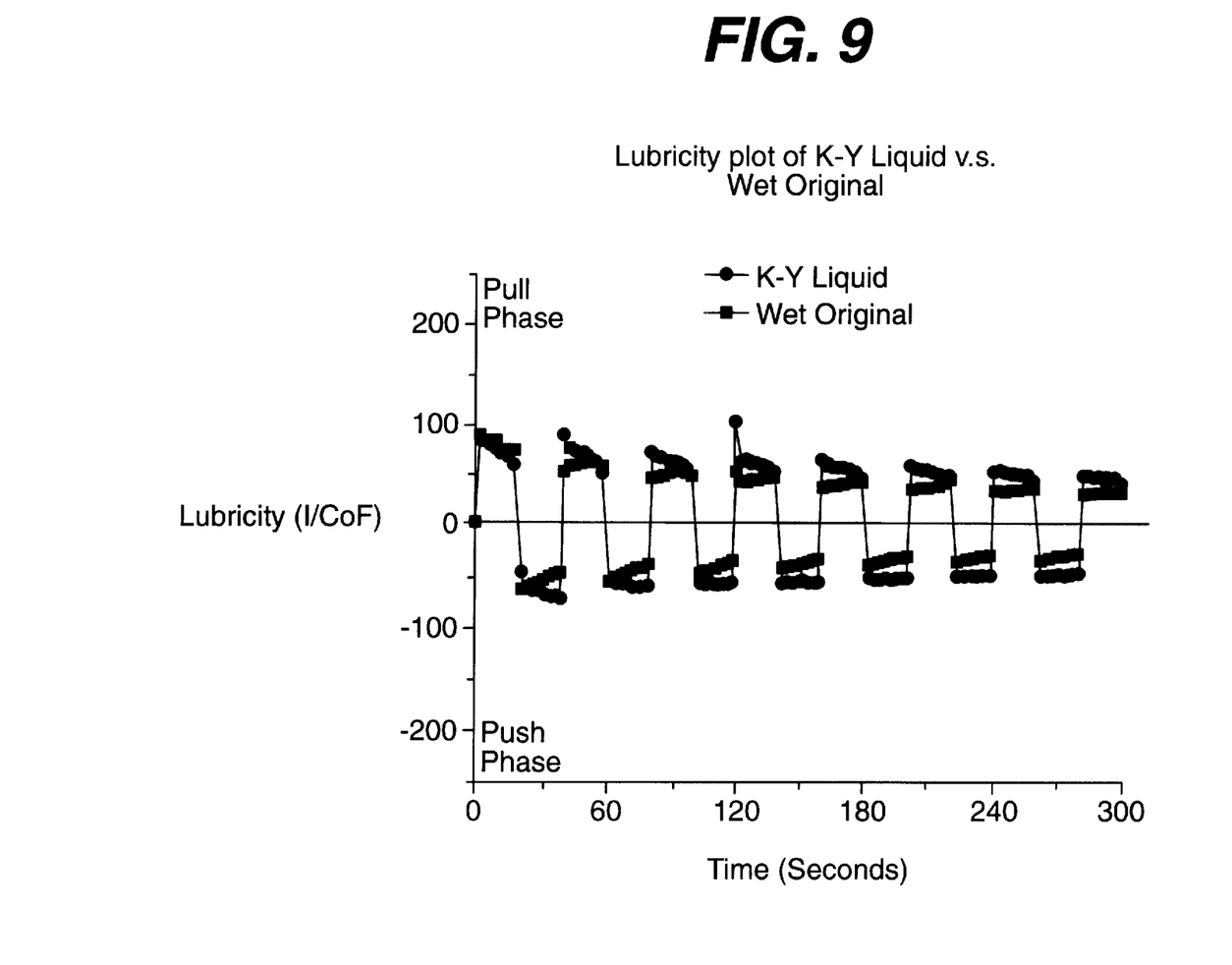
Figure 10:
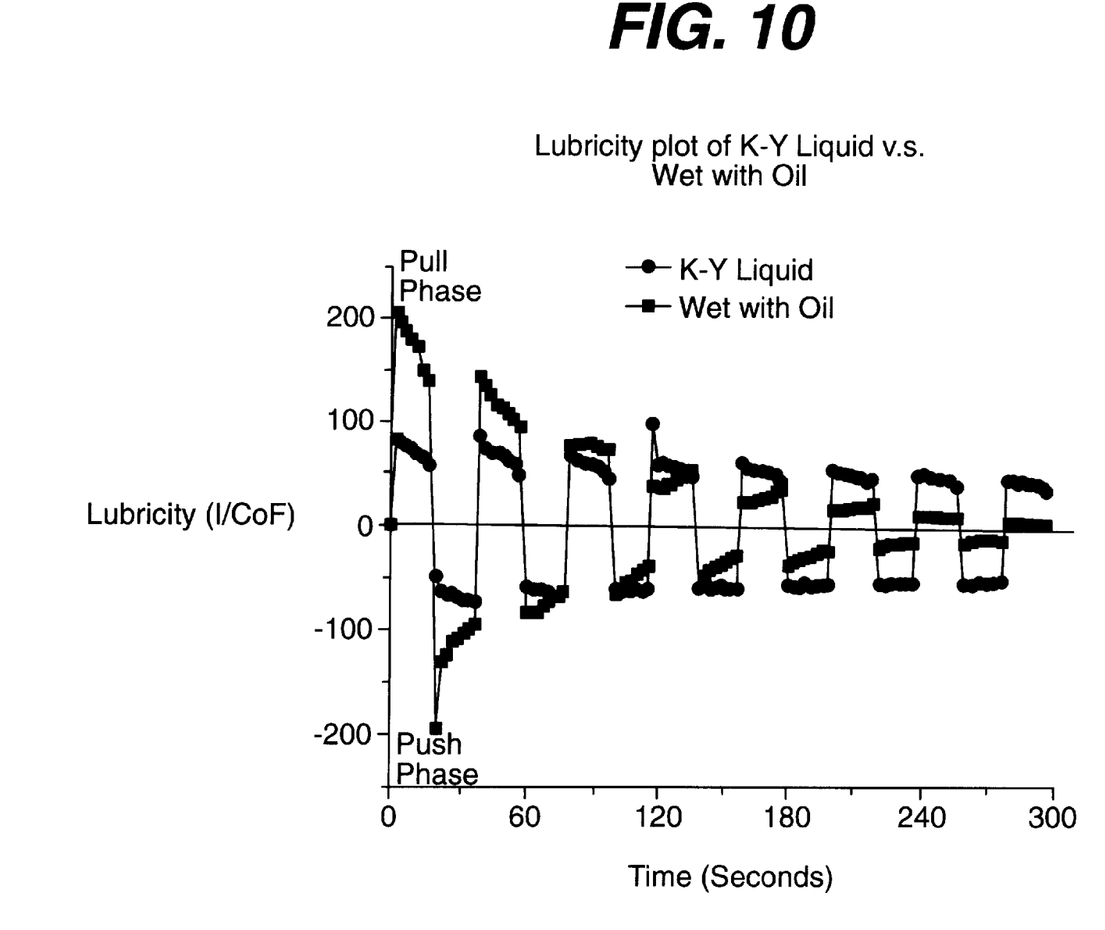
Figure 11:
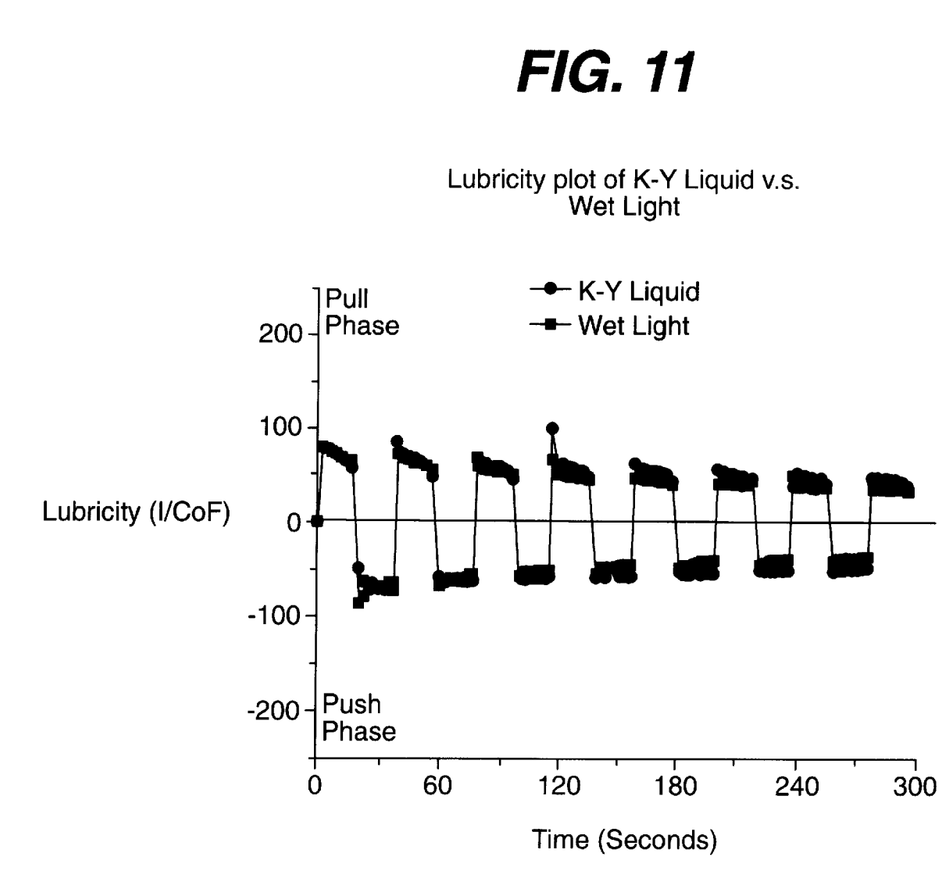
Figure 12:
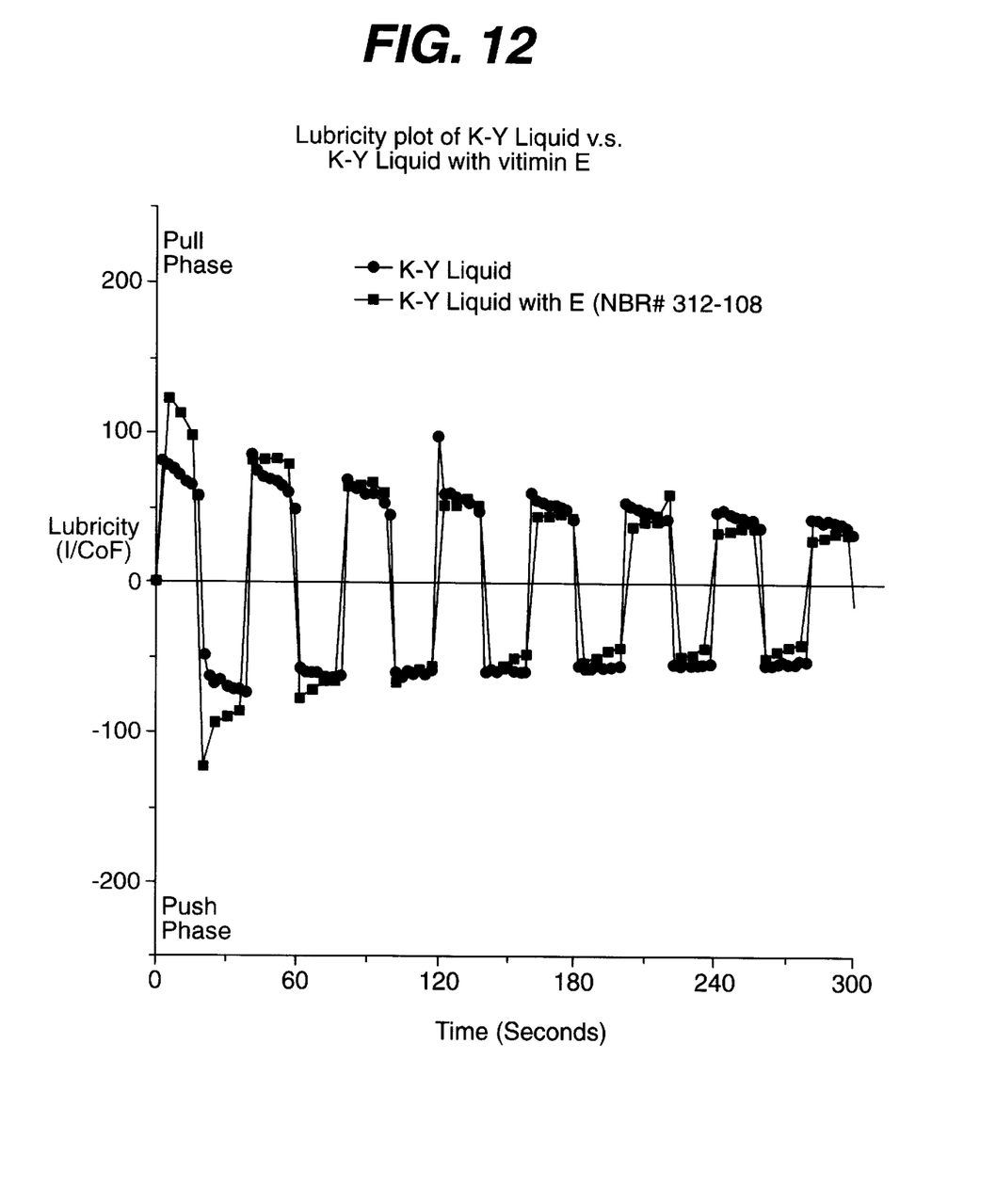
FIG. 12 is a graph comparing Relative Lubricity of a composition described in U.S. Pat. No. 5,885,591 and an embodiment of a composition prepared in accordance with this invention.

The relative lubricity of the composition described above in Example 2 was compared with that of K-Y Liquid® lubricant, a composition described in U.S. Pat. No. 5,885,591. As can be seen in the graph set forth in FIG. 12, the composition of Example 2 has as high relative lubricity as that of K-Y Liquid® lubricant.

EXAMPLE 5

Figure 13:
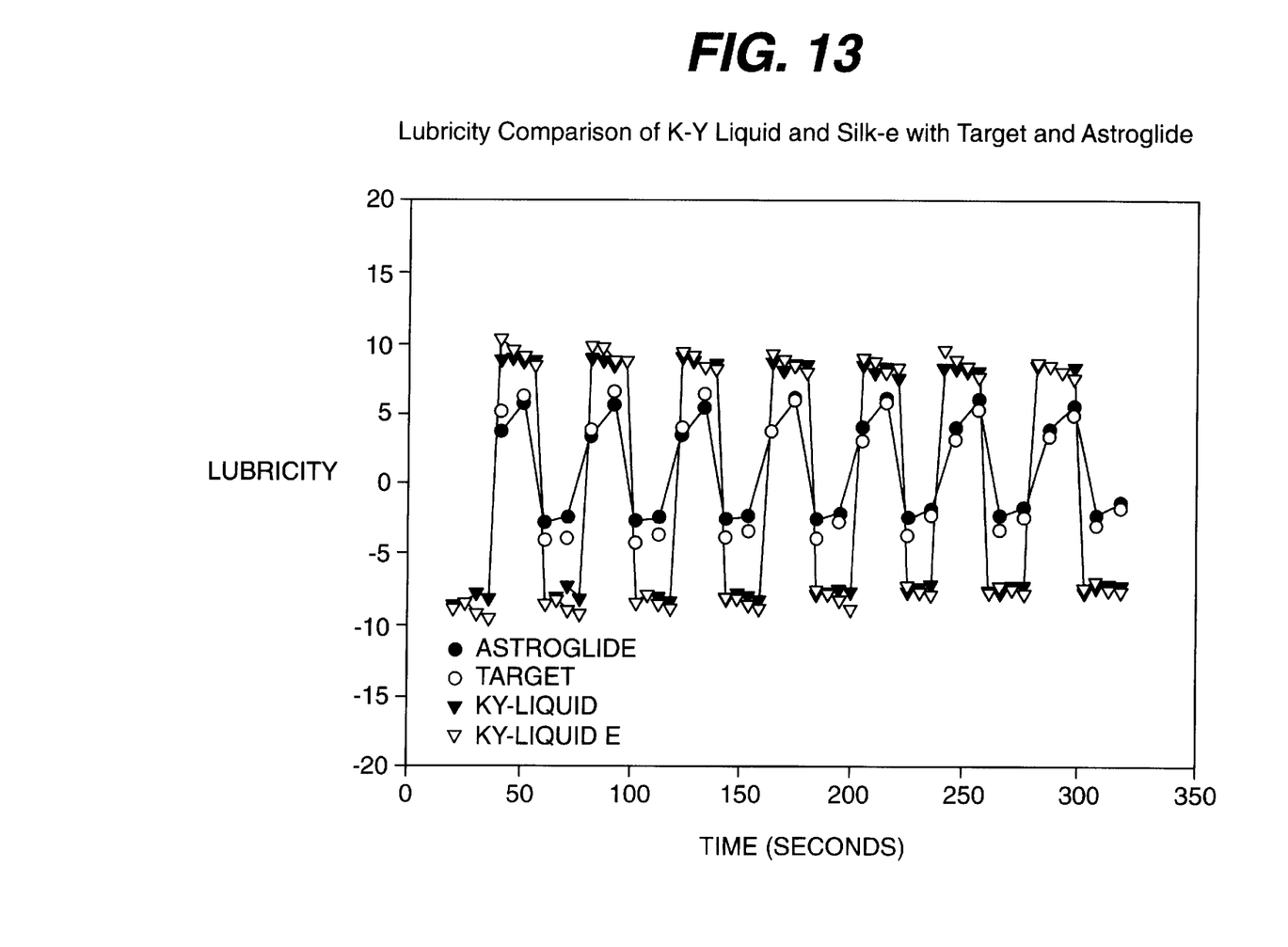
FIGS. 13 and 14 are graphs comparing Relative Lubricity of a composition described in U.S. Pat. No. 5,885,591 and an embodiment of a composition prepared in accordance with this invention with that of other test samples.
Figure 14:
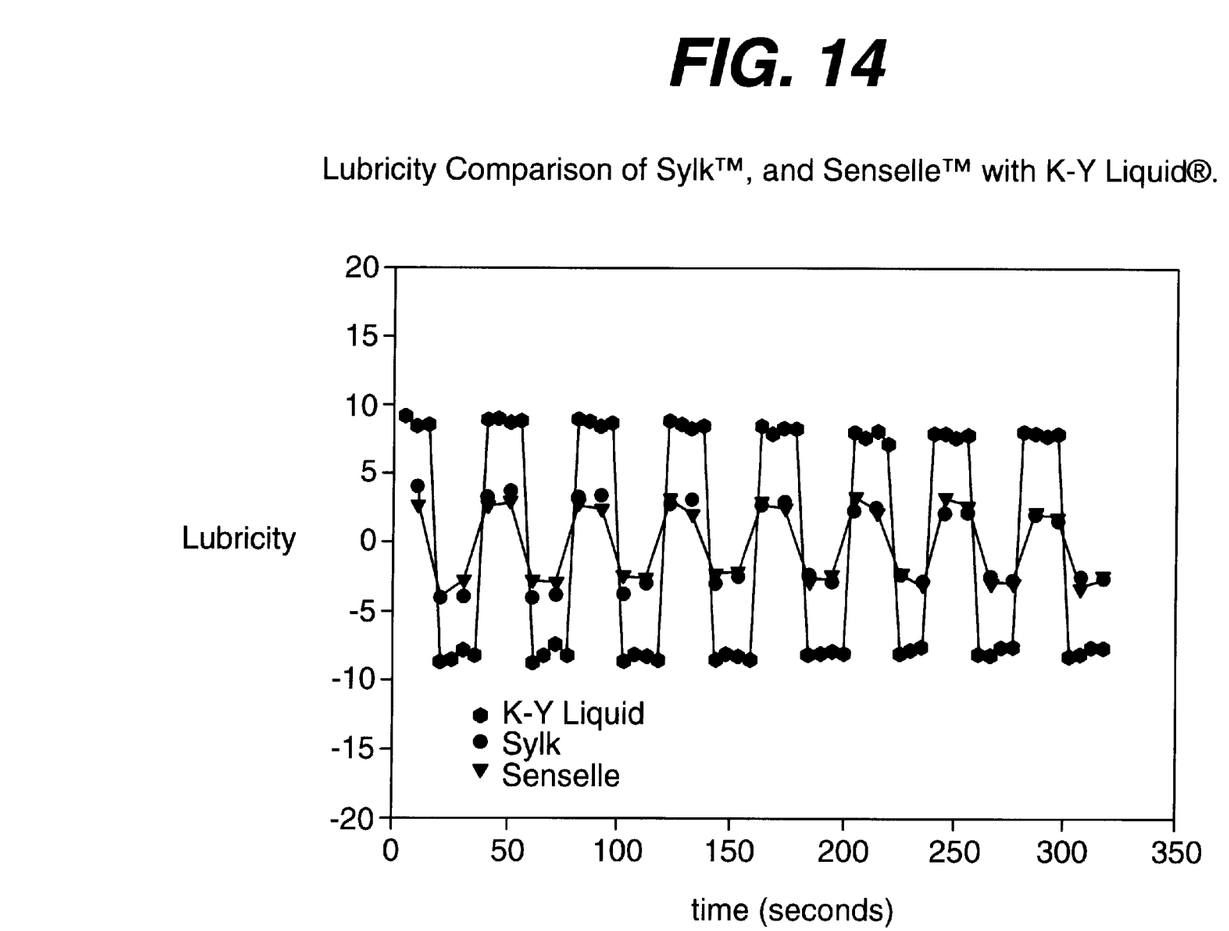

The relative lubricity of the composition described above in Example 2 and that of K-Y Liquid® lubricant were compared with Astroglide™ and Target™ lubricants. As can be seen in the graph set forth in FIG. 13, the compositions of Example 2 and K-Y Liquid® lubricant have considerably higher lubricities than those of the other comparative products.

What is claimed is:

1. A personal lubricant composition comprising at least one polyhydric alcohol which is water-soluble, a water-soluble polymer derived from cellulose, tocopherol or a tocopherol derivative, a nonionic emulsifier and water.

2. A composition according to claim 1 wherein said compositions are microemulsions.

3. A composition according to claim 1 where oil phase constitutes tocopherol only.

4. A composition according to claim 1 wherein said tocopherol is present in an amount from about 0.05% to about 2% by weight of the composition.

5. A composition according to claim 2 wherein the emulsion globules are not greater than 2 microns in size.

6. A composition according to claim 1 wherein the ratio of tocopherol to emusifier is from about 1:5 to 1:30.

7. A composition according to claim 1 wherein said composition is a clear and transparent.

8. A composition according to claim 7 wherein the clarity of the composition is at least 98%.

9. A composition according to claim 1 wherein said emulsifiers are selected from the group consisting of polyoxyethylene (20) sorbitan monostearate and the polyethylene glycol ether of isocetyl alcohol.

10. A composition according to claim 1 wherein said emulsifier is a polyalkylene-containing emulsifier.

11. A composition according to claim 1 wherein said composition has a lubricity of at least 30.

* * * * *